(12) United States Patent
Glenn, Jr.

(10) Patent No.: US 6,703,007 B2
(45) Date of Patent: *Mar. 9, 2004

(54) TOPICAL COMPOSITIONS COMPRISING FUNCTIONAL NUCLEOPHILES PROTECTED BY PHOSPHORUS-CONTAINING MOIETIES

(75) Inventor: Robert Wayne Glenn, Jr., Loveland, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,912

(22) Filed: Jan. 8, 1999

(65) Prior Publication Data

US 2002/0041855 A1 Apr. 11, 2002

(51) Int. Cl.[7] .................................................. A61K 7/06
(52) U.S. Cl. ..................... 424/70.1; 424/401; 424/70.2; 424/70.4; 424/70.5; 424/61
(58) Field of Search ............................... 424/70.5, 70.4, 424/70.2, 70.1, 61

(56) References Cited

U.S. PATENT DOCUMENTS

| | | | |
|---|---|---|---|
| 3,136,686 A | * 6/1964 | Beriger | 167/22 |
| 4,786,633 A | 11/1988 | Wagatsuma et al. | |
| 4,816,482 A | * 3/1989 | Oiry et al. | 514/513 |
| 4,859,460 A | 8/1989 | Mahieu et al. | 424/72 |
| 4,973,475 A | 11/1990 | Schnetzinger et al. | 424/70 |
| 5,030,756 A | 7/1991 | Deppert et al. | 564/291 |
| 5,087,733 A | 2/1992 | Deppert et al. | 560/147 |
| 5,206,013 A | 4/1993 | Deppert et al. | 424/71 |
| 5,211,942 A | 5/1993 | Deppert et al. | 424/70 |
| 5,254,335 A | 10/1993 | Deppert et al. | 424/70 |
| 5,350,572 A | 9/1994 | Savaides et al. | 424/71 |
| 5,523,080 A | * 6/1996 | Gough et al. | 424/70.12 |
| 5,525,332 A | 6/1996 | Gough et al. | 424/70.12 |
| 5,609,856 A | 3/1997 | Dubief et al. | 424/70.1 |
| 5,609,861 A | 3/1997 | Dubief et al. | 424/70.9 |
| 5,736,624 A | * 4/1998 | Bieniarz et al. | 530/391.1 |

FOREIGN PATENT DOCUMENTS

| | | | |
|---|---|---|---|
| WO | WO 94/26237 | 11/1994 | A61K/7/06 |
| WO | WO 96/03966 | 2/1996 | A61K/7/06 |
| WO | WO 96/15767 | 5/1996 | A61K/7/16 |
| WO | WO 98/38974 | 9/1998 | A61K/7/09 |

OTHER PUBLICATIONS

Remington's Pharmaceutical Sciences, 18th ed. 1990, pp. 1309–1313.
Abstract of JP 0–1226–805–A; Japan; Mar. 4, 1988.

* cited by examiner

Primary Examiner—Thurman K. Page
Assistant Examiner—Konata M. George
(74) Attorney, Agent, or Firm—Stephen T. Murphy; Tara M. Rosnell; Andrew A. Paul

(57) ABSTRACT

This invention relates to a topical composition for treating amino acid based substrates comprising a protected nucleophilic compound having the formula

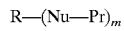

$$R-(Nu-Pr)_m$$

where R is a functional group, Nu is a nucleophile, and Pr is a phosphorus-containing protecting group, and m is an integer between 1 and 6. The invention further relates to systems which comprise this protected nucleophilic compound and an activating mechanism. The protected nucleophilic compounds of the present invention may be used in hair care compositions, textile care compositions, laundry care compositions, deodorant compositions, skin care compositions, cosmetic compositions, oral care compositions, and animal care compositions.

19 Claims, No Drawings

TOPICAL COMPOSITIONS COMPRISING FUNCTIONAL NUCLEOPHILES PROTECTED BY PHOSPHORUS-CONTAINING MOIETIES

TECHNICAL FIELD

The present invention relates to topical compositions for treating amino acid based substrates. The topical compositions comprise cosmetic or therapeutic actives that have been bound to a protected nucleophile which acts as a molecular 'hook' to impart "permanent" benefits to the amino acid based substrates. The amino acid based substrates can include, for example, proteinaceous materials such as keratin, as found in human hair, velis hair on skin, finger and toe nails; various animal body parts, such as horns, hooves and feathers; and other naturally occurring protein containing materials, e.g., such as silk and wool. Of particular interest are compositions which deliver and attach cosmetic actives to human hair.

BACKGROUND OF THE INVENTION

It is well known in the art that amino-acid based fibers, particularly hair, can be treated with agents that deliver one or more cosmetic benefits, such as conditioning, styling or setting. The conventional cosmetic products which have been known and used commercially have relied upon two key factors: deposition and retention. The cosmetic actives must first be physically deposited onto the hair fiber where the active imparts a benefit to a sufficient degree. Secondly, it is essential that the cosmetic actives be retained on the hair beyond the completion of the treatment. For example, when hair is rinsed to remove unwanted excess composition (e.g., a conditioner) a sufficient amount of the cosmetic active (humectant, moisturizer, etc.) remains bonded to the hair so as to maintain the desired cosmetic benefits.

The bonding of the cosmetic active material to the hair is generally of the nature of physico-chemical intermolecular forces, e.g., physisorption. Such physical forces comprise, for example, hydrogen bonding, electrostatic interactions, van der Waals interactions and the like. As an example, cationic cosmetic agents, generally of the quaternary ammonium type, are known to bond to hair by virtue of the interaction of their cations with anionic amino acid residues within keratin, e.g., glutamic acid, aspartic acid, cysteic acid etc. A major problem, however, with physisorption is the inevitable short lived retention of the cosmetic agent on hair. This is due to the relatively weak physical forces which bind the cosmetic to hair and which are easily disrupted by other treatments, e.g. washing. And, given the frequent need for treating hair, performance retention is difficult to achieve and generally does not last in excess of the period between washes.

One approach that has been disclosed in the art to overcome the above problem to provide truly durable or "permanent" cosmetic benefits to hair that are retained through multiple washes is to utilize molecular "hooks" to chemically bond cosmetic actives to hair keratin, e.g., chemisorption. Chemisorption results in a permanent juncture that is essentially resistant to physical wear from subsequent washings or physical abrasion. Two conventional approaches to achieve chemisorption comprise the use of either electrophilic reactive moieties or nucleophilic reactive moieties attached to the cosmetic active. Electrophilic reactive moieties are designed to react with nucleophilic functional groups present in hair and nucleophilic reactive moieties are designed to react with electrophilic functional groups within the hair to create a covalent bond.

U.S. Pat. No. 5,523,080 issued to Gough et al. on Jun. 4, 1996, U.S. Pat. No. 5,211,942 issued to Deppert et al. on May 18, 1993, and UK Patent Application GB2197887 published on Jun. 2, 1988, all disclose the use of electrophilic moieties. These electrophilic chemistries include the use of azalactone, (haloalkyl)trialkylammonium salts, and acyl halides. All of these molecular hooks react with hair via an electrophilic mechanism which necessitates sufficient nucleophilic functional groups present within the keratin structure with which to react. For hair, this poses a dilemma in that it is generally known that hair does not naturally possess a sufficient concentration of nucleophilic functional groups under consumer mild conditions to drive the reaction. However, it is also generally known that by chemically reducing the disulfide bonds present within the cystine amino acid residues of hair, in a manner analogous to cold waving, sufficient quantities of nucleophilic cystine residues can be produced. Pre-reduction of hair, to enable the chemical reaction with suitable electrophilic cosmetic actives, is illustrated below in reactions (a) and (b). Ker represents keratin protein, R—X represents an alkyl halide electrophilic cosmetic active, R represents a cosmetic agent and X⁻ is a halide anion such as bromide or chloride.

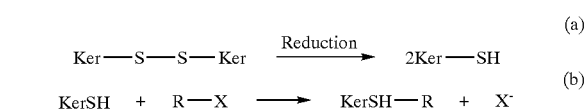

While electrophilic cosmetic actives have been demonstrated effective at providing durable cosmetic benefits to hair, the approach has disadvantages that arise from the required pre-reduction step. First, the reduction step is known to be a very harsh chemical process that imparts considerable damage to hair. Second, the effective reducing agents are typically mercaptans of low molecular weight and are odiferous. The pre-reduction process generates unpleasant malodor that remains on the hair for greater than a weeks time in most instances. Thirdly, in addition to unpleasant malodor and resulting hair damage, the required pre-reduction imparts an additional step to the process with resulting added inconvenience to the user.

U.S. Pat. No. 5,087,733 and U.S. Pat. No. 5,206,013 both issued to Deppert et al. on Feb. 11, 1992 and Apr. 27, 1993 respectively, as well as U.S. Pat. No. 4,973,475 issued to Schnetzinger and Ciaudelli on Nov. 27, 1990, describe the use of quaternary ammonium thiols which fall under the general class of nucleophilic reactive actives. Such nucleophilic actives are generally intended to react with cystine amino acid residues present within hair via formation of a mixed disulfide covalent linkage as is demonstrated in the chemical equation (c).

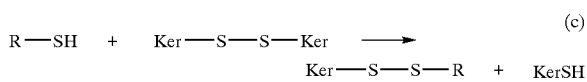

Ker represents keratin and R—SH represents a suitable nucleophilic active where R is a cosmetic agent and —SH representing a nucleophilic moiety. It is generally known that thiols are the preferred nucleophilic reactive moieties that possess enough reactive strength to chemically bond with the disulfide bond of cystine, Ker—S—S—Ker, under safe and mild consumer conditions (e.g., generally non toxic, less than 120 F, pH 2 to 11). Most other prospective nucleophilic molecular handles are either highly toxic (e.g., selenols), or are unreactive under mild conditions (e.g., alkoxides with pKa~15).

There are two major drawbacks to the use of nucleophilic thiols as reactive moieties to form covalent bonds with keratin. First, thiol nucleophilic moieties are known to be unstable in the presence of air. Atmosphere induced oxidation of the thiols to the corresponding, and unreactive, disulfide as is shown in the following equation (d) where R—S represents a suitable nucleophilic cosmetic active R being an alkyl cosmetic agent and —SH representing the nucleophilic moiety:

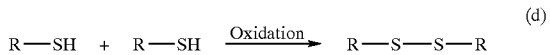
(d)

Such oxidative deactivation of the nucleophilic moieties severely limits their mode of usage. Thus, nucleophilic thiols are generally not stable enough to be utilized as such in a large majority of current product forms, i.e., re-sealable hair care packages widely used for shampoos, rinse-off conditioners etc. Second, the nucleophilic thiol moiety has very little affinity for hair keratin and has very low aqueous solubility, both of which hinder its performance in generating durable cosmetic benefits, especially when attached to hydrophobic, insoluble cosmetic actives, i.e., hydrocarbon conditioners, in-soluble polymers etc.

Despite major efforts, however, the art has not yet provided molecular "hooks" that provide durable cosmetic benefits to hair that last beyond twenty shampoos and which do not necessitate the damaging cold waving of hair, i.e. hair reduction, while being oxidatively stable in solution for long term storage in a variety of currently used product forms, e.g., rinse of conditioners, two-in-one shampoos, etc.

Phosphorus-containing electrophilic groups have been used in the pharmaceutical sciences to increase efficiency of radioactive drugs which employ thiols as free radical scavangers within the body. In U.S. Pat. No. 4,816,482, issued to Oiry on Mar. 28, 1989, herein incorporated by reference, the phosphorus-containing electrophilic group is used to improve the solubility of, and simultaneously protect, a radioprotector.

The present invention is concerned with the application of classes of phosphorus compounds containing at least one divalent sulfur atom in a masked form which can be released to provide a SH or S⁻ group which functions as a molecular handle capable of binding to proteins. These phosphorus compounds are refer to herein as "hooks". It has now been discovered that, surprisingly, such "hooks", R—(Nu—Pr)$_m$ wherein Pr represents a phosphorus moiety, provide durable cosmetic benefits that last beyond twenty shampoos without necessitating the damaging cold-waving of hair. It has also been discovered that the molecular "hooks" of the present invention surprisingly provide improved oxidative stability versus conventional thiols by virtue of the phosphorus thiol ester bond that reduces the oxidative susceptibility of the sulfur atom(s). Furthermore, it has been found that these molecular "hooks" significantly outperform conventional nucleophilic thiol hooks in providing durable cosmetic benefits. While not being bound to theory, the latter observed effect is believed to be due to the unexpected high affinity for keratin provided by the polarizable phosphorus electrophilic groups which offer improved solubility and possibly even electrostatic interaction with the charged keratinaceous substrate. Presumably, such greater affinity affords enhanced diffusion and adsorption to the fiber by the cosmetic active enabling greater opportunity for binding.

The molecular "hooks" of the present invention enable the achievement of durable cosmetic benefits that are resistant to cleansing or shampooing from essentially a non-damaging process that is void of cold waving. The binding of the cosmetic actives provided by the molecular 'hooks' of the present invention is to such a degree of durability that the measured cosmetic benefits will remain in hair for multiple shampoo cycles, e.g. eight to twenty or more. While not being restricted to theory, it is believed that such a high degree of durability is due to the formation of covalent bonds between the cosmetic active and the keratinaceous subtrate. A possible reaction for the formation of covalent bonds is via the formation of a mixed disulfide with the existing disulfide bonds within keratin as is illustrated below, reaction (e), wherein R represents the cosmetic active, Ker represents the keratin protein, S represents the sulfur atom and P represents the phosphorus electrophilic group:

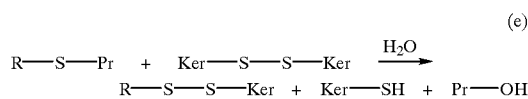
(e)

Based on theory, the above sulfur-phosphorus thioester bond would need to be broken via some form of activation yielding the reactive unmasked thiol which would then be capable of forming a mixed disulfide with keratin disulfides via nucleophilic displacement. Such activation could be accomplished via hydrolysis or by a separate nucleophile that can be imparted by the substrate itself or from a separate composition. Such hydrolytic or nucleophilic attack can itself be enhanced by application of a suitable energy source, manipulation of the pH, the use of specialized solvent systems, the use of dispersing aids, the use of lewis acid catalysts etc. However, it has been discovered that, surprisingly, the molecular 'hooks' of the present invention are capable of providing for durable binding with keratin without the need for such a prior or simultaneous activation process. While not being bound to theory, it is believed that the keratin itself could be activating the sulfur-phosphorus thioester bond to enable the observed durable benefits. The resulting free phosphorus electrophilic group may or may not undergo decomposition reactions. The byproducts of the activation of the sulfur-phosphorus thioester bond will usually be removed from the substrate by washing.

SUMMARY OF THE INVENTION

This invention relates to a topical composition for treating amino acid based substrates, wherein the topical compositions comprise a protected nucleophilic compound having the formula

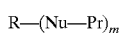

where R is a functional group, Nu is a nucleophile, and Pr is a phosphorus-containing protecting group, and m is an integer between 1 and 6. The invention further relates to systems which comprise these protected nucleophilic compounds and an activating mechanism. The protected nucleophilic compounds of the present invention may be used in hair care compositions, textile care compositions, laundry care compositions, deodorant compositions, skin care compositions, cosmetic compositions, oral care compositions, and animal care compositions.

DETAILED DESCRIPTION OF THE INVENTION

The present invention relates to topical compositions which provide attachment of functional groups to amino acid based substrates.

As used herein, "cystine containing, amino acid based substrates" are proteinaceous materials which contain the cystine amino acid in its amino acid sequence. The phrase "amino acid sequence" refers to a specific configuration of the amino acids comprising a protein. The compositions of the present invention can be used to attach functional groups to materials such as keratin, as found in human and animal hair, and nails; various animal body parts such as horns, hooves and feathers; and other naturally occurring protein containing materials, such as wool and silk.

The topical compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Protected Nucleophilic Compound

The compositions of the present invention comprise a protected nucleophilic compound having the formula

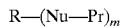

R—(Nu—Pr)$_m$ where R is a functional group, Nu is a nucleophile, Pr is a phosphorus containing protecting group, and m is an integer ranging from about 1 to about 6, preferably from about 1 to about 3, more preferably equal to 1 or 2, and most preferably equal to 1.

Typically, the protected nucleophilic compounds of the present invention are present in the compositions of the invention in an amount from about 0.000001% to about 30%, preferably from about 0.0001% to about 25%, more preferably from 0.01 to about 20%, even more preferably from about 0.1% to about 10%, and most preferably from about 1% to about 5%, by weight of the composition. Suitable ranges of amounts will generally depend upon the functional group in question. For example, hair conditioners that are modified with the molecular 'hooks' of the present invention will normally be present from about 0.01% to 10% by weight of the composition, and hair styling agents that are modified such as cationic conditioning polymers or polyisobutylene will normally be present from about 0.01 to 10% by weight of the composition, perfluoropolyether materials that are modified may be present from about 0.000001 to 0.01% by weight of the composition, and other film forming polymers that are modified may be present from about 0.01 to 2% of the composition.

Each of the three components of the protected nucleophic compounds are discussed in detail as follows:

Nucleophile

The protected nucleophilic compound from about 1 to about 6, preferably from about 1 to about 3, more preferably equal to 1 or 2, and most preferably equal to 1, nucleophiles, Nu, each paired with one protective group. The nucleophiles of the present invention can comprise sulfur, selenium, nitrogen, or oxygen. Sulfur is the preferred nucleophile.

Phosphorus Containing Protecting Group

The protected nucleophilic compound comprises from about 1 to about 6, preferably from about 1 to about 3, more preferably equal to 1 or 2, and most preferably equal to 1 phosphorus-containing protecting groups, Pr, each paired with one nucleophile. The phosphorus containing protecting groups of the present invention are phosphorus-linked tri-, tetra-, penta- or hexa-coordinated moieties, including derivatives of phosphoric, phosphonic, phosphinic, phosphorous, phosphonous, phosphinous, phosphoranoic, phosphoranedioic, phosphoranetrioic, phosphoranetetraoic, or phosphoranepentoic acids. The phosporus-linked moieties can be represented by the following formulas:

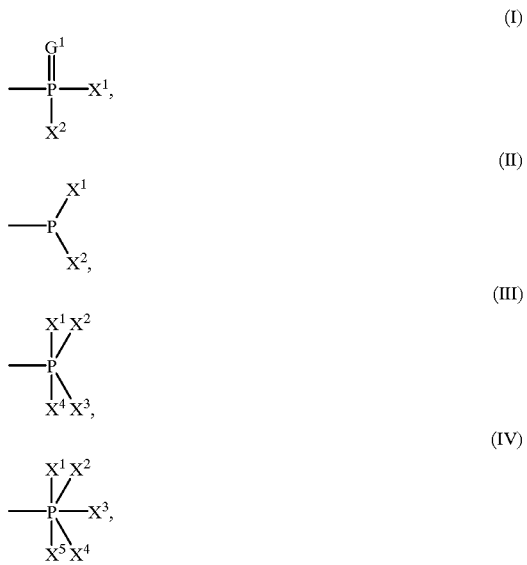

in which:

$G^1$ is O, S, Se, $NA^1$, $NOA^1$, $NA^1A^2$, $CA^1A^2$, $PA^1$, $PA^1A^2A^3$, $PG^2A^1$;

$G^2$ is $G^1$;

$A^1$, $A^2$, and $A^3$ each represent, independently from one another, a monovalent group which can be the cosmetic active group, R, or H or any of the following: a straight chain, branched chain or mono- or poly-cyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, fluoro-substituents such as poly- or per-fluoro substitution.

$X^1$, $X^2$, $X^3$, $X^4$, and $X^5$ represent, independently from one another, electron withdrawing or electron donating groups with Hammett sigma para values between −1.0 and +1.5. The electron withdrawing or electron donating groups comprise carbon-linked groups defined above as $A^1$, $A^2$, and $A^3$; sulfur-linked groups including $SA^1$, SCN, $SO_2A^1$, $SO_3A^1$, $SSA^1$, $SOA^1$, $SO_2NA^1A^2$, $SNA^1A^2$, $S(NA^1)A^2$, $S(O)(NA^1)A^2$; oxygen-linked groups including $OA^1$, OCN, $ONA^1A^2$; nitrogen-linked groups including $NA^1A^2$, $NA^1A^2A^{3+}$, NC, $NA^1OA^2$, $NA^1SA^2$, NCO, NCS, $NO_2$, N=$NA^1$, N=$NOA^1$, $NA^1$CN, N=C=$NA^1$, $NA^1NA^2A^3$, $NA^1NA^2NA^3A^4$, (where $A^4$ is defined similarly to $A^1$, $A^2$, and $A^3$), $NA^1$N=$NA^2$; other miscellaneous groups including COHal, $CON_3$, $CONA^1_2$, $CONA^1COA^2$, C(=$NA^1$)$NA^1A^2$, CHO, CHS, CN, NC, Hal, and derived groups that connect one or more of $X^1$, $X^2$, $X^3$, $X^4$, or $X^5$ via a ring system. Hal is F, Cl, Br, or I.

H is hydrogen, O is oxygen, N is nitrogen, C is carbon, S is sulfur, Cl is chlorine, Br is bromine, I is iodine, F is fluorine, R is any functional group as describe above.

The invention also relates to polyphosphorus containing acid analogs,

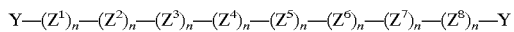

or cyclic polyphosphorus containing acid analogs,

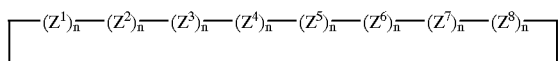

wherein, $Z^1$, $Z^2$, $Z^3$, $Z^4$, $Z^5$, $Z^6$, $Z^7$, and $Z^8$ are

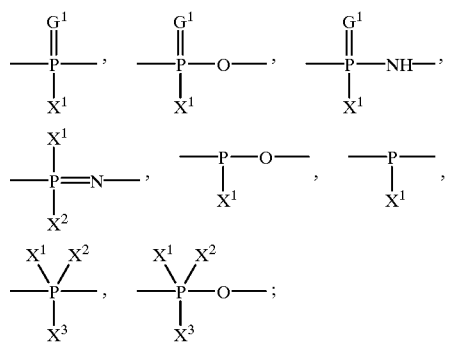

or non-phosphorus linking groups such as —N=N—, —NA$^1$—NA$^2$—, —S—S—, —S—S—S—, —S—S—S—S, or similar analogs, Y is a terminal group having the formula:

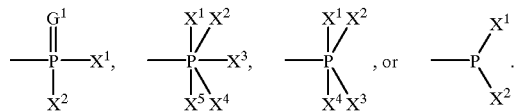

$X^1$, $X^2$, $X^3$, $X^4$, and $X^5$ are defined as above, with the additional requirement that at least one X must be SR.

The n's can vary, independently from one another, from 0 to about 10.

The invention also includes salts of $X^1$, $X^2$, $X^3$, $X^4$ or $X^5$ wherein the counterion can be Li, Na, K, Mg, or Ca.

The functional group, R, of the present invention (hereinafter discussed in detail) may be monofunctionalized such that the protected nucleophilic compound carries a single nucleophile-protecting group combination, or it may be bi- or multi-functionalized, such that the protected nucleophilic compound carries two or more, preferably less than 3 nucleophile-protecting group combinations. The latter may be useful for example in achieving a greater degree of chemical bonding of the cosmetic agent to the substrate or for generating bonds between adjacent features of the substrate, e.g. producing a cross-linking effect. The latter may be employed to improve the strength or tensile properties of keratinaceous fibers or for enhancing the degree of hair setting compared with current hair setting methods.

In the preferred compounds of this invention, the phosphorus-linked moieties are derivatives of phosphoric acid of general formula (I) wherein $G^1$ is O or S, and $X^1$, $X^2$ is $OA^1$ or $SA^1$. Principal among the preferred phosphorus electrophiles having the general formula (I) include phosphorothioc acid, diethyl phosphorothioate and dimethyl phosphorothioate:

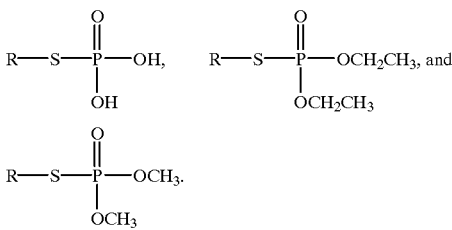

It is understood that within the scope of this invention that when we refer to the R—SH structure, it is intended to represent both the protonated form, R—SH, as well as the anion, R—S$^-$. Equally, it is to be understood that when we refer to an acid structure as in phosphorothioic acid (I), it is intended to represent both the protonated acid form (I), as well as the corresponding salt variations (II and III),

(I)

(II)

(III)

wherein M is a suitable counterion including but not limited to Li, Na, K, Mg, or Ca.

Functional Group

The functional group, R, suitable for inclusion in the present invention may be any compound that imparts one or more visual, tactile or other cosmetic beneficial effects on proteinaceous materials such as keratin, wool, and silk. Any cosmetic compound may be included as a functional group in the compositions of the present invention as long as the compound can be modified to contain at least one thiol ester linkage to a suitable phosphorus electrophile as described below.

Suitable functional groups include but are not limited to antimicrobial compounds, UV-absorbing compounds, skin conditioning agents, hair conditioning agents, hair repair agents, hair styling agents, hair dyes, scalp treatment agents, anti-inflammatory compounds, antioxidants, coloring agents, perfumes, oral care actives, skin moisturizers, pharmaceutical agents, antidandruff agents, insect repellents, moisturizers, humectants, pearlescent and/or opacifying materials, fabric care actives, pet grooming actives, fabric anti-wrinkling agents, shrink-resistant actives, laundry care actives, hard surfaces actives, textile actives, textile dyes, water-proofing agents, cationic polymers, cationic surface modifiers, hydrophobic surface modifiers, anionic surface modifiers, absorbents, antifungal agents, insecticidal agents, textile color guards, nail actives such as enamel and polish, eyelash actives and mascara, antiperspirant and deodorant actives, anti-acne actives, odor control actives, fluorescent actives, bleaching agents, enzymes, antibodies, dispersing aids, emollients, stabilizers, anti-static agents, anti-seborrhea agents, brighteners, fluorescent dyes, softeners, cross-linkers, and mixtures thereof.

Examples of suitable antimicrobials which can serve as the functional group include but are not limited to derivatives of phenol, cresol, hydroxybenzoates, Triclosan®, Tricarban®, chlorhexidine, metal salts (e.g. zinc citrate, sodium zinc citrate, zinc pyridinethione, and stannous pyrophosphate) sanguinarine extract, metronidazole, quaternary ammonium compounds (chlorhexidine digluconate, hexetidione, octenidine, alexidine), halogenated bisphenolic compounds such as 2,2'-methylenebis-(4-chloro-6-bromophenol), and salicylanilide.

Examples of suitable UV-absorbing materials which can serve as the functional group include but are not limited to derivatives of benzoates, oxybenzones, cinnamic acid and PARSOL MCX esters.

Examples of suitable skin conditioners or moisturizers which can serve as the functional group, include but are not limited to derivatives of alpha-hydroxy acids, polyols, hyaluronic acid, petrolatum, vegetable oils, esters of fatty acids, and mineral oil. Such skin conditioners or moisturizers are bound to the velis hairs present on the skin, and not the skin directly, to achieve the long lasting skin benefits.

Examples of suitable anti-inflammatory agents which can serve as the functional group include but are not limited to corticosteroids or salicylates.

Examples of suitable antioxidants which can serve as the functional group include but are not limited to ascorbates and gallates.

Examples of suitable hair conditioners which can serve as the functional group include but are not limited to intact or modified proteins, such as hydrolyzed keratin, collagen, elastin, hemoglobin, silk, rice, soy, wheat protein, corn, fibronectin, reticulum, serum protein, wheat gluten, peptides and peptide derivatives; amino acids; hydroxylated fats; glycinates; silicone polymers, such as siloxane gums and resins, volatile or non-volatile silicone oils, amino-(or other) functional silicones, and other silicone-containing polymers; hydrocarbon based conditioners including $C_8$–$C_{30}$ alkyl, alkenyl, modified alkyl or modified alkenyl, branched alkyl and branched alkenyl groups as well as long chain alkyl groups substituted with various non-ionic, cationic or anionic functional groups including quats, amines, amides, esters, hydroxyls, carboxylates and the like; polysaccarides or monosaccharides, and alkyl cationic conditioning polymers such as cationic derivatives of guar gum and cellulose ether derivatives; and herb or other plant extracts, essential oils etc.

Examples of suitable hair styling agents which can serve as the functional group include but are not limited to film-forming polymers such as polyvinylpyrrolidone/vinyl acetate copolymer; styling copolymers comprising silicone macromonomers, U.S. Pat. Nos. 5,618,524 and 5,658,557, cationic polymers, such as those disclosed in GB-A-2161172 (Beecham), GB-A-2122214 (Unilever) and GB-A-2050166 (L'Oreal); and hydrocarbon polymers, such as polyisobutylene; perfluoro-aliphatic and perfluoro-aromatic compounds.

Examples of suitable coloring agents which can serve as the functional group include but are not limited to phenol, naphthols, azo derivatives; vegetable dyes, metallized dyes, nitrobenzene dyes, quinone-imine dyes, basic dyes, quaternary dyes, and oxidation dyes.

Examples of suitable fragrances that can serve as the functional group include but are not limited to phenols such as menthyl salicylate, thymol, and vanillin.

Examples of suitable cationic polymers that can serve as the functional group include but are not limited to derivatives of quaternary ammonium salts of hydroxyethylcellulose, cationic copolymers of acrylic acid and acrylamide, cationic guar polymers, copolymers of vinylimidazolium methochloride and vinylpyrrolidone, polyethylenimines, and other cationic polymers and resins known to those skilled in the art.

Examples of suitable oral care active agents that can serve as the functional group include but are not limited to anti-caries agents such as amine flourides, monosodium fluorophosphate, casein; plaque buffers such as urea, calcium lactate, calcium glycerophosphate; anti-plaque agents; agents for alleviating sensitive teeth, e.g. potassium and strontium salts, particularly those of carboxylic acids; materials that form films and block pores; oral pharmaceutical actives, (e.g. buprofen, flurbiprofen, aspirin and indomethacin); biomolecules such as peptides, antibodies and enzymes; anti-tartar agents; agents for treating bad breath such as zinc salts; and anti-calculus agents (e.g. alkalimetal pyrophosphates, hypophophite-containing polymers, organic phosphonates, and phosphocitrates).

Examples of suitable pharmaceutical agents that can serve as the functional group include but are not limited to medicinal agents, metabolic agents and other therapeutic agents of benefit in treating the human body.

Examples of antidandruff agents that can serve as the functional group include but are not limited to zinc pyridinethione, octopirox®, climbazole.

An example of odor control actives that can serve as the functional group include the class of cyclodextrins. In addition to trapping odors on the substrate, the cyclodextins can plausibly be utilized to deliver hydrophobic molecules to the substrate such as perfumes that can be liberated slowly.

Other non-limiting classes of beneficial cosmetic actives include sealants, binders, resins, adhesives, waxes, drying oils, varnishes, and latex finishes which comprise urethanes, polysulfides, acrylics, butyl polymers, maleated oils, cellulosics, starches etc.

The functional group preferrably used in the present compositions is dependent on the product form desired. Hair care compositions preferrably use hair conditioners, hair styling agents, coloring agents, sunscreens, fragrances, anti-dandruff agents, or mixtures thereof as the functional group. Preferrable functional groups in textile care compositions include coloring agents, odor control actives, sealants, fragrances, and mixtures thereof. Cosmetic compositions preferrably comprise coloring agents, sealants, resins, varnishes, latex finishes, and mixtures thereof. Oral care compositions preferrably comprise anti-caries agents, plaque buffers, anti-plaque agents, agents for alleviating sensitive teeth, materials that form films and block pores, oral pharmaceutical actives, biomolecules, anti-tartar agents, agents for treating bad breath, anti-calculus agents, and mixtures thereof as functional groups. Pharmaceutical composition preferrably select functional groups from the group consisting of medicinal agents, metabolic agents, therapeutic agents, anti-inflammatory compounds, and mixtures thereof. Animal care composition preferably comprise antimicrobial agents, insect repellants, grooming actives, and mixtures thereof as functional groups.

In hair care compositions, the preferred functional groups are selected from the group consisting of hair conditioners, hair styling agents, coloring agents, sunscreens, fragrances, antidandruff agents, and mixtures thereof. In textile care compositions, the preferred functional groups are selected from the group consisting of coloring agents, odor control actives, sealants, fragrances, and mixtures thereof. In cosmetic compositions, the preferred functional groups are selected from the group consisting of coloring agents, sealants, resins, varnishes, latex finishes, and mixtures thereof. In oral care compositions, the preferred functional groups are selected from the group consisting of anti-caries agents, plaque buffers, anti-plaque agents, agents for alleviating sensitive teeth, materials that form films and block pores, oral pharmaceutical actives, biomolecules, anti-tartar agents, agents for treating bad breath, anti-calculus agents, and mixtures thereof. In animal care compositions, the preferred functional groups are selected from the group consisting of antimicrobial agents, insect repellants, grooming actives, and mixtures thereof.

Optional Activating Mechanisms

As explained above, the molecular 'hooks' of the present invention may be activated via a number of mechanisms either before, during or after the application of the topical compositions containing the protected nucleophilic compound to the substrate. Various embodiments of the present invention are systems which comprise both the topical composition herein with an activating mechanism.

Such activation could be achieved via hydrolysis by the use of a mechanism to manipulate the pH of the environment surrounding the compound. Such pH adjusting mechanisms may include acidic or alkaline solutions. Whether acidic or alkaline mechanisms are required is dependent on the protecting group used. Hydrolysis may also be achieved via simply mixing the compound, delivered in its purified form or from a non-aqueous solution, with water.

Furthermore, the molecular 'hook' could be activated by coming in contact with a suitable nucleophile. Such nucleophiles include, but are not limited to, nitrogen-containing functional groups, for example hydroxyl groups, oxygen-containing functional groups, for example hydroxyl groups, and sulfur-containing functional groups, for example thiol groups. For instance, the solution containing the 'hook' compound could be inter-mixed with a separate solution containing a nucleophile including reducing agents such as ammonium thioglycolate or sodium bisulfite, either before, during or after application of the compound to the substrate.

Conversely, the 'hook' compound could be activated by nucleophilic groups present in the substrate itself as in the case of hair that has been reduced or cold waved, i.e. hair that has been treated with a reducing agent either prior to or simultaneous to the application of the 'hook' compound. The resulting activated thiol 'hook' could then react directly as a nucleophile with keratinaceous disulfides or oxidatively with the nucleophilic functional groups present in the substrate, e.g. with free thiol groups that were formed during cold waving or reduction. Of course, the latter process could be accelerated or enhanced via the addition of oxidation reagents, i.e. peroxide as in the neutralization step of cold waving of hair.

The activation could also be accented via heat or a suitable energy source. For instance, the energy source could be applied to the composition for a sufficient time period to activate the protecting group either before, during or after the composition is applied to the substrate. The energy source may include various types of electromagnetic radiation including ultraviolet, visible, near infrared, infrared, far infrared or microwave radiation.

Other various adjuncts that could possibly influence the activation and/or the performance of the "hook" compounds of the present invention include, but are not limited to, lewis acids such as zinc acetate, tin chloride, zinc chloride, zinc stearate, titanium ethoxide, and aluminum tosylate, metal salts such as zinc sulfate, and magnesium sulfate, chelators such as tetrasodium EDTA, disodium EDTA, ionic species capable of ion-pairing including anions, cations, quats, amphoterics zwitterions etc, dispersing aids such as anionic surfactants, non-ionic surfactants, anionic surfactants, amphoteric surfactants, and zwitterionic surfactants, keratin swelling aids such as ammonia, amines, urea, phosphoric acid, acetic acid and other swelling aids known to those skilled in the art, and solvent systems wherein the individual solvent molecules are nucleophiles themselves as defined above.

Another embodiment of the present invention comprises a kit comprising the system comprising the topical compositions of the present invention and either a pH manipulating mechanism or a nucleophile mechanism, and a package comprising a first and second chamber; wherein the topical composition is packaged in and delivered out of one chamber and the activation mechanism is packaged in and delivered out of the second chamber.

Other Optional Ingredients

The topical composition according to the invention can also typically include an acceptable vehicle to act as a dilutant, dispersant, or carrier for the protected nucleophilic compounds in the composition, so as to facilitate the distribution of the protected nucleophilic compounds when the cosmposition is applied to the keratinaceous substrate, i.e., hair, nails, wool, skin etc.

Vehicles other than water can include liquid or solid emollients, solvents, humectants, thickeners and powders. Examples of each of these types of vehicle, which can be used singly or as a mixture of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow lard, olive oil, palm kernel oil, rapeseed oil, safflower seed oil, eveneing primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoro etane, propane, butane, isobutane, dimethyl ether, carbon dioxide, nitrous oxide;

Solvents include, but are not limited to, ethyl alcohol, propanol, butanol, low molecular weight poly(ethylene oxide), glycerin, propylene glycol, 2-butoxyethanol, amyl alcohol, octanol, decanol, acetone, acetic acid, butyl acetate, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran, amyl lactate, benzyl alcohol, 1,2-dichloropropane, 1,4-butanediol, butyl alcohol, thiodyglycol, 1,2-hexanediol, diacetone alcohol, hexylene glycol, betaphenylethyl alcohol, cyclohexanol, furfuryl alcohol, ethyl benzoate, nicotinic acid, picolinic acid, 3-amyloxy-1,2-propanediol, tetrapropyl urea, tetraethyl urea, 1,1-dipropyl-3,3-diethyl urea, cyclohexanone, acetophenone, propylacetate, diethylmalonate, pyridine-2-carbinol and the like;

Powders, such as chalk, talc, fullers earth, kaolin, starch, gums, colloidal silica, sodium polyacrylate, tetra alkyl and/or trialkyl aryl ammonium smectites, chemically modified magnesium aluminum silicate, organically modified montmorillonite clay, aluminum silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the composition and can, in the absence of other cosmetic adjuncts, form the balance of the composition.

The cosmetic compositions according to the invention may be provided in any suitable physical form, for example as low to moderate viscosity liquids, lotions, milks, mousses, sprays, gels, foams, aerosols, and creams. These compositions may be produced by procedures well known to the skilled artisan. The cosmetic compositions can be used in various manners as other known compositions in the art including but not limited to various rinse-off and leave-on applications such as hair shampoos, skin cleansers, skin lotions, hair conditioners, styling sprays, hair mousses, two-in-one shampoos, fabric softeners, lotions, nail polishes, hair serums, hair dyes, hair waving, etc. The contact time between the cosmetic composition of the present invention and the substrate varies between 10 seconds and about 1 hour, preferably between 20 seconds and 30 minutes, more preferably between 30 seconds and 15 minutes.

The cosmetic composition of the present invention can be formulated as a fluid, lotion, fluid cream or cream having a viscosity from 500 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for hand or finger operation. When the composition is a cream, it can simply be stored in a non-deformable bottle or squeeze container, such as a tube or a lidded jar.

The cosmetic product or composition of the present invention may include an activator as described above. In such a case, the inventive composition must be designed to prevent pre-mature activation of the protected nucleophilic compound prior to use. For instance, the protected nucleophilic compound and the activator may be placed in separate chambers in a dual chamber package, or either of the 'hook' compound or the activator can be placed within shear sensitive (or other induced release) capsules which rupture prior or during use. Alternatively, the protected nucleophilic compound and the activator can be placed in separate packages to enable pre-mixing or sequential application by the consumer.

Conversely, the cosmetic active of the present invention can be supplied in the purified form, i.e., as a powder, crystal, wax, gum or liquid. The purified cosmetic active could be intermixed with any of the above suitable carriers either prior to or simultaneous to the usage by the consumer. For instance, the purified cosmetic active could be placed within a compartment that is separated from the carrier by a barrier wall. Upon usage, the barrier wall could be broken, disrupted or even removed to enable the purified cosmetic active to come in contact with and inter-mix with the carrier.

The cosmetic composition of the present invention comprises at least one of the above described phosphorus-containing organosulfur functionalized cosmetic agents, together with any additional ingredients which are normally to be found in cosmetic treatment compositions for use on hair, skin, or other substrates such as other fibers, textiles, fabrics, or the like. One or more of the phosphorus-containing organosulfur functionalized cosmetic agents may be used, the use of two or more being beneficial for example where a combination of cosmetic benefits is wanted, each derivable from a different cosmetic agent species.

While aqueous or aqueous/alcoholic solution based compositions, or possibly organic-based compositions, in which one or more phosphurus-containing organosulfur functionalized cosmetic agents are dissolved by the solution are preferred, the compositions if desired or appropriate may comprise stable emulsions of the one or more functionalized cosmetic agents which are designed to be water insoluble. In both of these cases, conventional means for achieving successful depositions of the active(s) may be required.

The cosmetic composition according to the invention may include optional benefit materials and cosmetic adjuncts, as long as the benefit materials or the adjuncts do not substantially reduce or eliminate the performance of the phosphorus-containing organosulfur functionalized cosmetic agent. The additional ingredients may include, for example coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, dyes, coloring agents, enzymes, antibodies, preservatives, viscosity enhancers, gelling agents, chelators, silicones or other emulsifying agents, and other common adjuvants well known to those skilled in the art.

Nonlimiting examples of anionic lathering surfactants useful in the compositions of the present invention are disclosed in McCutcheon's, *Detergents and Emulsifiers*, North American edition (1990), published by The Manufacturing Confectioner Publishing Co.; McCutcheon's, *Functional Materials*, North American Edition (1992); and U.S. Pat. No. 3,929,678, to Laughlin et al., issued Dec. 30, 1975, all of which are incorporated by reference.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and mixtures thereof. Mixtures of anionic surfactants can be used effectively in the present invention.

Suitable nonionic surfactants include polyoxyalkylene alcohol surfactants, especially alkyl polyethyleneglycol ethers, alkyl polypropyleneglycol ethers, alkyl polyethylene glycol esters, and alkyl polypropylene glycol esters and mixtures thereof.

Suitable amphoteric surfactant components for use in the shampoo composition herein include those which are known for use in shampoo compositions or other personal care cleansing composition, and which contain a group that is anionic at the pH of the shampoo composition. Concentration of such surfactant components in the shampoo composition preferably ranges from about 0.5% to about 20%, preferably from about 1% to about 10%, more preferably from about 2% to about 5% by weight of the composition. Examples of amphoteric surfactants suitable for use in the shampoo compostion herein are described in U.S. Pat. No. 5,104,646 (Bolich Jr. et al.), U.S. Pat. No. 5,106,609 (Bolich Jr. et al.), which descriptions are incorporated herein by reference. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378.

Other amphoteric surfactants, sometimes classified as zwitterionic surfactants, such as betaines can also useful in the present invention. Such zwitterionics are considered as amphoterics in the present invention where the zwitterionic has an attached group that is anionic at the pH of the composition. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH$_2$)$_3$ radical is attached to the nitrogen atom of the betaine are also useful in this invention. Most preferred for use herein is cocoamidopropyl betaine.

If desired or as necessary, one or more additional cosmetic benefit agents may also be included in the compositions of the invention, for example to modify the overall cosmetic benefit or combination of benefits imparted to the substrate treated with the composition. Suitable additional cosmetic benefit agents include the following:

(i) conditioning agents, i.e., materials which impart one or more visual or tactile benefits such as softness, smoothness, shine, non-flyaway, anti-static, ease of dry and/or wet combing, e.g., cationic surfactants, cationic polymers, volatile and/or non-volatile silicones or derivatives thereof, quaternary ammonium salts having at least one long chain alkyl or alkenyl group, protein hydrolysates, quaternized protein hydrolysates, perfluoropolyether materials, fatty alcohols, and mixtures thereof;

(ii) styling/setting/bodying agents, i.e., materials which give enhanced body and fell to the hair or other fibers or enable them to hold a given shape or style, e.g., various polymers, gums and resins, for example adhesive and/or resinous hydrocarbon materials such as peralk(en)yl hydrocarbon materials, silicone/siloxane gums or resins, waxes, chitosan and derivatives, salts and complexes thereof, and mixtures thereof;

(iii) fiber straightening agents;

(iv) colourants and dyeing agents;

(v) antidandruff agents, e.g., zinc pyridinethione, octopirox (trade mark), climbazole;

(vi) sun-protective materials, e.g. sunscreens, especially UV absorbers;

(vii) hair growth promoters or regulators, e.g. diacylglycerols, glucarolactams, glucarolactones, Minoxidol (trade mark);

(viii) moisturizers, e.g. 2-hydroxyalkanoic acids, acid soap and complexes thereof, and other emollients, occlusives, humectants;

(ix) pearlescent and/or opacifying materials;

(x) oils, e.g. silicone oils, oleic acid, hydrocarbons, isopropyl myristate, oleyl alcohol, oleates, squalene, sunflower seed oil, rapeseed oil, other plant derived oils, mineral oil;

(xi) proteins, vitamins, nutrients, stimulants, antiradicals, astringents;

(xii) herb or other plant extracts, essential oils etc.

(xiii) antimicrobial agents, e.g. antibacterial or anti-infestive agents;

(xiv) other adjunct materials commonly used in cosmetic compositions, e.g., buffering and/or pH adjusting agents, perfumes, colorings, preservatives, proteins etc.

(xv) anti-malodor agents as those disclosed to treat post-perm odors in U.S. Pat. No. 5,554,364 and EP0610892.

(xvi) highly substantive polymers and other moieties including polyethylenimines (PEI's) such as those included within the Polymin series supplied by BASF.

(xvii) metal salts comprising alkaline earth metals such as magnesium and calcium, transition metals such as zinc, manganese and copper, and the group IIIA metals such as Al. The use of these metal salts for hair treatment is disclosed in WO9609030 and WO9703640 where they are claimed to form metal-sulfur bonds with the hair for use in hair styling and restyling. Such metal salts could conceivably be employed to complex and interact with the cosmetic active of the present invention. Such interactions should not interfere too greatly with the performance of the cosmetic actives and could potentially positively influence the performance, i.e., metals could complex with the sulfur atom within cosmetic active and facilitate or induce activation in the form of thiol release.

(xviii) chelating agents including disodium EDTA and tetrasodium EDTA. Chelators could enhance the diffusion and adsorption by binding to and removing metals present in hard water such as calcium and magnesium. Such hard water ions could conceivably complex with certain ionized "hooks" of the present invention electrostatically and inhibit their solubility.

(xix) hydrotropes such as ammonium xylene sulfate. For instance, if the "hooks" of the present invention are incorporated within a surfactant matrix, hydrotropes could improve performance by freeing up the "hook" compounds during dilution to facilitate improved binding to the substrate.

(xx) dispersing aids which may encompass, but are not limited to, non-ionic surfactants, amphoteric surfactants, and ionic surfactants. If the "hooks" of the present invention are incorporated within a non-aqueous matrix, dispersing aids could plausibly be utilized to prevent precipitation during usage.

(xxi) Ion-pair ingredients. For certain ionic "hooks" of the present invention, compounds could be employed that ion-pair with the "hooks" including, but not limited to cations, anions, quaternized ammonium compounds, amphoteric compounds, and metals. Such charged species could be utilized to manipulate the diffusion, adsorption and the binding of the "hook" compounds of the present invention.

The pH of the compositions of the present invention is frequently important in achieving optimized chemisorption of the phosphorus-containing organosulfur functionalized cosmetic agent. The most suitable pH for a given composition may depend principally on the type and structure of the phosphorus-containing organosulfur molecular 'hook' as it pertains to activation. For instance, many of the phosphorus-containing organosulfur molecular 'hooks' can be activated for improved performance via pH catalyzed hydrolysis. In these cases, the pH of the composition would need to be such that the molecular 'hook' is not activated prior to usage. As described above, during usage the pH of the composition containing the molecular 'hook' can be manipulated, i.e., via inter-mixing with separate pH activating composition, such that the molecular 'hook' is activated during or immediately prior to usage.

The phosphorus-containing organosulfur molecular 'hooks' of the present invention are to be used within a pH range between 1 and 12, preferably between 3 and 10. In the cases wherein the phosphorus-containing organosulfur hooks are activated at all of the above pH's, the composition would need to be non-aqueous and essentially free of water or moisture to such a degree that prohibits significant hydrolysis induced activation prior to usage. As such, the water imparted to the composition during usage from the shower, bath or from the wetted substrate could provide the activation required to optimize the resulting chemisorption.

As mentioned above, it has surprisingly been found that certain phosphorus-containing organosulfur moleculear 'hooks' are not activated hydrolytically at pH's within the above ascribed relevant range while still providing durable benefits on hair. For these compounds, the pH of the composition is irrelevant in as much as the composition pH suits the cosmetic active, R.

Processes for Preparing the Protected Nucleophilic Compounds

The compounds of the invention can be prepared by any of a number of procedures known to those skilled in the art. The methods for the preparation of the preferred derivatives of phosphorothioic acid or phosphorothioate esters are known. There are two general methods to prepare these compounds: 1. Reaction of phosphorus compounds with sulfur compounds by formation of the P—S bond; or 2. Reaction of PS⁻ with RX or a double bond by formation of the S—C bond.

EXAMPLE I

Preparation of O,O-diethyl-S-hexadecylphosphorothioate

Reaction Sequence:

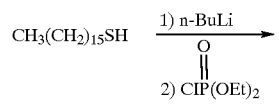

-continued

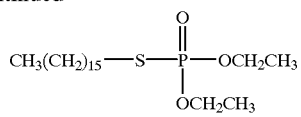

A solution of n-butyllithium was prepared by adding n-butyllithium (960 ml, 2.4 mol, 2.5M solution in hexanes) to anhydrous THF (6.0 L) at −5 to 0° C. over 30 minutes, under argon, with stirring. To this solution was added hexadecanethiol (600 g, 2.32 mol) over 1.5 hours at −5° C. The resulting white, pasty suspension was stirred (−5° C.) for 1 hour, then diethyl chlorophosphate (445 g, 2.58 mol) was added over 30 minutes at temperatures not exceeding 0° C. The resulting solution was stirred ~−5° C. for 1 hour, allowed to warm to room temperature and then stirred for an additional 2 hours. The resulting colorless solution was concentrated in vacuo to an oil which contained a white precipitate. The solution was diluted with hexanes (3 L) and stored overnight. The precipitated solid was filtered off and the filtrate was concentrated to a clear oil. The crude oil was purified on a silica gel pad (2.5 kg) eluted with 0–30% ether/hexanes. The appropriate fractions containing the product were combined and concentrated in vacuo to yield 647 grams of colorless oil suitable for further transformation. An additional reaction was performed to give 65 grams of the purified O,O-diethyl-S-hexadecylphosphorothioate ester. Calc. % C, 60.88; % H, 10.98; % S, 8.12; Found % C, 61.15; % H, 10.96; % S, 7.92; The $^1$H NMR, $^{31}$P NMR and IR agree with the proposed structure.

EXAMPLE II

Preparation of S-hexadecylphosphorothioic Acid

Reaction Sequence:

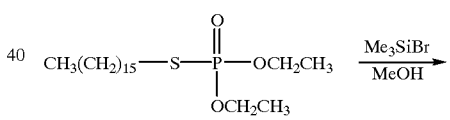

To a stirred solution of the O,O-diethyl-S-hexadecylphosphorothioate ester (645 grams, 1.635 mol) in CH$_2$Cl$_2$ (3.0 L), cooled to −2° C., was added bromotrimethylsilane (626 g, 4.09 mol) in a thin stream over 30 minutes. The resulting solution was stirred cold (~0° C.) for 1 hour, then at room temperature for 48 hours. The reaction mixture was concentrated in vacuo to an oil which was further diluted with MeOH (1.5 L) and concentrated again to a solid. The solid was dissolved in warm (~40° C.) methanol (2.8 L), concentrated to approximately half volume, and cooled in an ice bath for 2 hours. The precipitated solid was collected and washed with cold MeOH (2×100 ml). The wet cake was dissolved in warm (~40° C.) hexanes (1.8 L), clarified by filtration, then cooled at −3 to 4° C. for 2 hours. The white, crystalline solid was filtered and washed with cold (~0° C.) hexanes (3×120 ml). The resulting solid was air dried overnight then dried in vacuo at 40° C. to constant weight, yielding 412 grams of product. A total of 850 grams of target S-hexadecylphosphorothioic acid was prepared in 47% overall yield from a total of 1388 grams of 1-hexadecanethiol. This yield was obtained, in part, by re-purification of the second crop material. Calc. % C, 56.77; % H, 10.42; % S, 9.47; Found % C, 57.52; % H, 10.61; % S, 9.67; m.p. 84–85° C. The $^1$H NMR, $^{31}$P NMR and IR agree with the proposed structure.

EXAMPLE III

Preparation of S-[2-[(2,4-dinitrophenyl)amino]-ethyl] phosphorothioic Acid

Reaction Sequence:

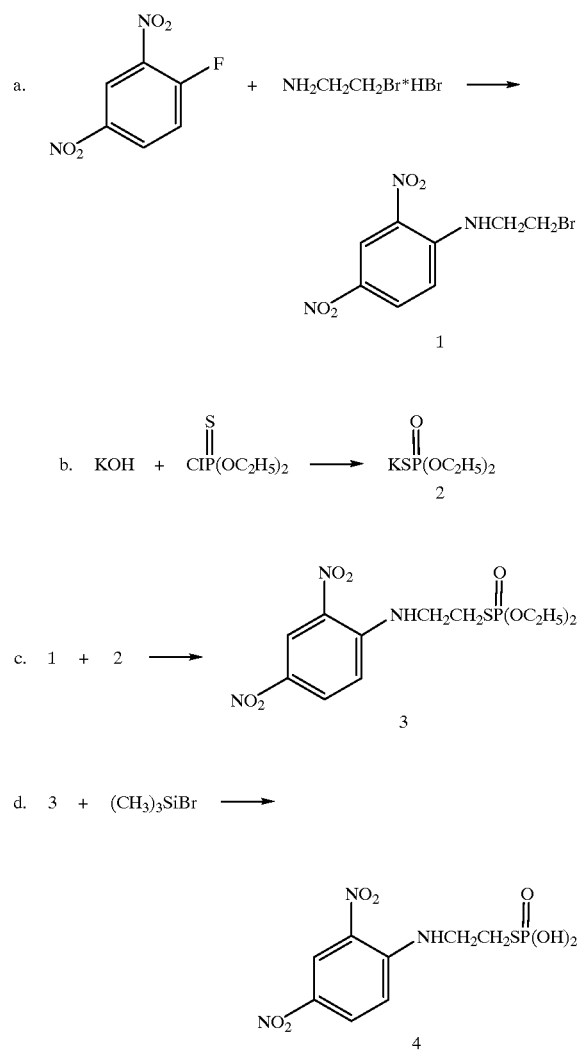

N-(2-bromoethyl)-2,4-dinitroaniline (1):

Triethylamine (340 ml, 2.44 mol) was added over 2 hours to a well stirred mixture of 2-bromoethylamine hydrobromide (265 g, 1.26 mol) and 2,4-dinitrofluorobenzene (222 grams, 1.19 mol) and tetrahydrofuran (1.2 L) while cooling in cold water. After the addition was completed the by now yellow mixture was stirred for 4 hours at ambient temperature. TLC (silica gel, EtOAc-hexanes, 7:18) did not show any 2,4-dinitrofluorobenzene. The mixture was filtered, and the residue was washed with THF (3×800 ml); the last washing was colorless. The THF was evaported in vacuo to a dark syrup which was dissolved in $CH_2Cl_2$ (500 ml). This solution was applied to silica gel (1.5 kg) in $CH_2Cl_2$. The column was eluted with $CH_2Cl_2$ (8 L). The product fractions (~3 L) were concentrated in vacuo to ~800 ml. The mixture was heated to dissolve the product, then diluted with hexanes (~300 ml). After crystallization was complete the bright yellow solid was collected and washed with $CH_2Cl_2$-hexanes (600 ml, 1:3) to afford the product as a bright yellow solid, 249 grams (72%). (Single bright-yellow spot on silica gel when developed with EtOAc-hexanes 7:18). Potassium diethyl thionophosphate (2):

Diethyl chlorothionophosphate (240 grams, 1.27 mol) was added dropwise to a solution of 85% potassium hydroxide (165 grams, 2.50 mol) in absolute ethanol (1.5 L). The reaction mixture was warmed until the ethanol began to reflux. After stirring for 2 hours, the suspension was filtered and the filtrate was concentrated to one-fourth of the original volume. Addition of dry $Et_2O$ (ca. 2 L) caused the product to precipitate. The suspension was suction filtered and the solid was recrystallized from hot absolute ethanol (400 ml) and dried in vacuo at 100° C. to give 66.4 grams (25%) of product (2); mp 198–200° C. (uncorrected); lit. mp 197° C. O,O-diethyl-S-[2-[(2,4-dinitrophenyl)amino]-ethyl] phosphorothioate ester (4):

A mixture of the above bromo compound (1) (51.3 grams, 0.176 mol), potassium diethyl thionophosphate (2) (37.4 grams, 0.179 mol) and acetone (500 ml) was stirred and heated at reflux for 4.5 hours. The mixture was cooled in an ice bath and filtered; the precipitated KBr was washed with acetone (1.2 L). The combined filtrates were evaporated to a red syrup which later crystallized. The solid was dissolved in $CH_2Cl_2$ (~200 ml) and this solution was applied to silica gel (1.5 kg) in $CH_2Cl_2$. The column was eluted with $CH_2Cl_2$ (12 L) then with $CH_2Cl_2$-EtOAc (9:1, 6 L). The yellow product fractions were filtered and evaporated in vacuo (35–40° C.) to give a bright yellow solid; 62.0 grams (92.4%).

S-[2-[2,4-dinitrophenylamino]ethyl] phosphorothioic Acid:

Bromotrimethylsilane (55 ml, 0.42 mol) was added dropwise (1 hour) to a stirred, cold (ice bath) solution of the above diethyl ester (61.4 grams, 0.161 mol) in $CH_2Cl_2$ (250 ml) under argon. The cooling bath was removed and the solution was stirred at room temperature for 48 hours. The solution was evaporated in vacuo then re-evaporated with dry methanol portions (100 ml, and 2×250 ml). The yellow solid was stirred with $CH_2Cl_2$ (200 ml), and then filtered to provide 21.8 grams of a bright yellow product (dried in vacuo at 40–45° C.). The filtrate was concentrated in vacuo to a solid. This solid was stirred with $CH_2Cl_2$ (250 ml) and collected to give an additional 22 grams of product (dried in vacuo at 40–45° C.). The two solids were combined and analyzed; mp 124–126° C. Calc. % C, 29.73; 10% H, 3.12; % N, 13.00; % S, 9.92; Found. % C, 29.87; % H, 3.18; % N, 12.82; % S, 9.80. The $^1$H NMR, $^{31}$P NMR and IR agree with the proposed structure. $^1$H NMR showed about 0.3% of the mono ethyl ester precurser. No other impurities were observed.

Other examples of the protected nucleophilic compounds of the present invention are:

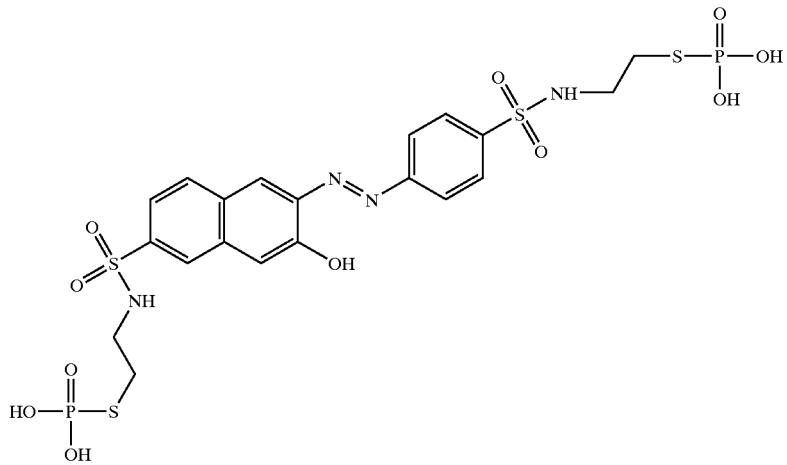

EXAMPLE IV

Modified F&DC Yellow #6

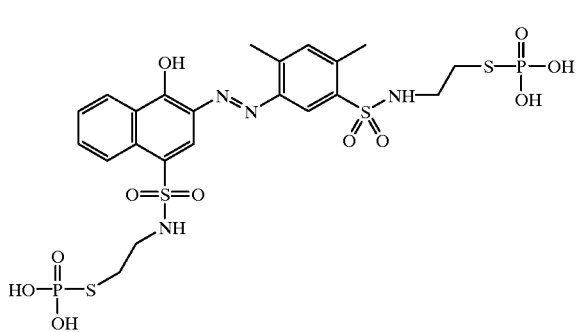

EXAMPLE V

Modified F&DC Red #4

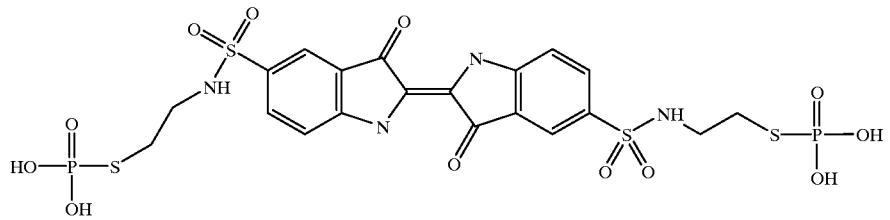

EXAMPLE VI

Modified Indigo Carmine

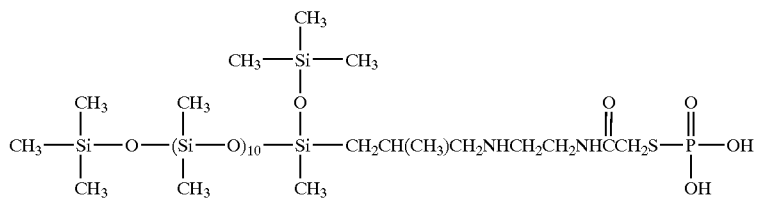

EXAMPLE VII

Modified Siloxane

These compounds are made by synthesis methods known in the art, including but not limited to those described above and those described in Sokolowska-Gaida, J. and Freeman, H., Dyes and Pigments (1990) Vol. 14, pp 35–48 and European Patent Application EP 0437099 A1 Published by Dow Corning Corp. (Inventors: Halloran, D. J., et al.).

Methods of Using the Protected Nucleophilic Compounds of the Present Invention

The method of use of the various protected nucleophilic compounds is dependent on the product form utilized. The use would be as typically used for the product chosen.

The protected nucleophilic compound of the present invention can be used in a variety of ways in hair care compositions. For example, the compounds of the present invention is applied directly to the hair in a alcohol/solvent/water solution comprising:

| | |
|---|---|
| S-hexadecylphosphorothioate | 3.00% |
| Isopropanol | 25.00% |
| 1,2 Hexane diol | 25.00% |
| Water | 47.00%. |

After application, the hair is washed or rinsed to remove excess solvent. The resulting bound hexadecyl group provides long lasting conditioning benefits to the hair.

A second conditioner composition using the protected nucleophilic compounds of the present invention comprises:

| | |
|---|---|
| O, O-diethyl-S-hexadecylphosphorothioate | 3.00% |
| Isopropanol | 25.00% |
| 1,2 Hexane diol | 25.00% |
| Water | 47.00%. |

Alternately, a conditioning composition using the protected nucleophilic compounds of the present invention comprises:

| | |
|---|---|
| The Modified Siloxane of Example VII | 5.00% |
| Isopropanol | 50.00% |
| Water 45.00%. | |

A representative dye composition using the protected nucleophilic compounds of the present invention comprises:

| | |
|---|---|
| S-[2-[(2,4-dinitrophenyl)amino]-ethyl] phosphorothioic acid | 5.00% |
| Isopropanol | 50.00% |
| Water 45.00%. | |

A second dye composition using the protected nucleophilic compounds of the present invention comprises:

| | |
|---|---|
| S-[2-[(2,4-dinitrophenyl)amino]-ethyl] phosphorothioic acid | 1.00% |
| Urea 10.00% | |
| Cocamidopropyl Betaine | 0.80% |
| Water 88.20% | |

The protected nucleophilic compounds may also be added to technologies currently well known in the art to treat substrates such as hair, teeth, finger nails, textiles, and animal fur. Nonlimiting examples of such compositions are described in the references below, each of which are incorporated herein by reference in its entirety:

Shampoos—U.S. Pat. No. RE 34,584 (Grote et al.) issued Apr. 12, 1994; U.S. Pat. No. 4,345,080 (Bolich) issued Aug. 17, 1982; U.S. Pat. No. 4,379,753 (Bolich) issued Apr. 12, 1983; and U.S. Pat. No. 4,705,681 (Maes et al.) issued Nov. 10, 1987.

Hair conditioners—U.S. Pat. No. 4,387,090 (Bolich) issued Jun. 7, 1983; U.S. Pat. No. 5,674,478 (Dodd et al.) issued Oct. 7, 1997; and U.S. Pat. No. 5,750,122 (Evans et al.) issued May 12, 1998.

Hair styling compositions—U.S. Pat. No. 5,166,276 (Hayama et al.) issued Nov. 24, 1992; U.S. Pat. No. 5,565,193 (Midha et al.) Oct. 15, 1996; and U.S. Pat. No. 5,658,557 (Bolich et al.) issued Aug. 19, 1997.

Hair coloring compositions—U.S. Pat. No. 4,197,865 (Jacquet et al.) issued Apr. 15, 1980, U.S. Pat. No. 4,125,367 (Bugaut et al.) issued Nov. 14, 1978, U.S. Pat. No. 5,114,429 (Junino et al.) issued May 19,1992, and U.S. Pat. No. 5,279,620 (Junino et al.) issued Jan. 18, 1994.

Mascara compositions—Commonly assigned U.S. patent application Ser. No. 08/951,285 (Alwatarri et al.), filed Oct. 16, 1997, (Attorney's Docket 6345C); Ser. No. 08/757,538 (Bartholomey et al.), filed Nov. 27, 1996 (Attorney's Docket 6397); and Ser. No. 09/121,138 (Alwatarri et al.), filed Jul. 23, 1998 (Attorney's Docket 5654C2); and in PCT Application Nos. US96/04154, published Oct. 31, 1996; US97/19786, published May 7, 1998; and US97/21890, published Jun. 4, 1998.

Nail polish and nail polish subcoat compositions—U.S. Pat. No. 4,179,304 (Rossomando) issued Dec. 18, 1979, U.S. Pat. No. 5,538,717 (LaPoterie) issued Jul. 23, 1996, and U.S. Pat. No. 5,639,447 (Patel) issued Jun. 17, 1997, U.S. Pat. No. 5,567,428 (Hughes) issued Oct. 22, 1996.

Toothpaste compositions—U.S. Pat. No. 4,254,101(Denny) issued Mar. 3, 1981, and U.S. Pat. No. 4,314,990 (Denny et al.) issued Feb. 9, 1982, and PCT Application No. WO 96/15767 (Unilever PLC) published May 30, 1996.

Textile dye and treatment compositions—

Other typical compositions are found in *Cosmetic and Toiletry Formulations,* 2nd Ed, Flick, E. W., Noyes Publications (N.J.), *Harry's Cosmeticology, 7th* Ed., Harry, R. G., Wilkinson, J. B., and Moore R. J., Chemical Pub. Co. (NY) (1982); and *Cosmetics, Science and Technology, 2nd* Ed., Balsam, M. S. and Sagarin, E. S., Wiley-Interscience (NY) (1972) (3 volumes).

Other embodiments of the present invention comprise a system comprising a topical composition containing the protected nucleophilic compound and an activating mechanism. For example the dye composition:

| | |
|---|---|
| S-[2-[(2,4-dinitrophenyl)amino]-ethyl]phosphorothioic acid | 1.00% |
| Urea | 10.00% |
| Cocamidopropyl Betaine | 0.80% |
| Water | 88.20% | can be applied simultaneously with a 5% solution of thioglycolic acid. A preferred embodiment is a kit wherein the dye solution and the thioglicolic acid are packaged in separate chambers of a dual chamber package and delivered simultaneously from the package.

What is claimed is:

1. A hair care composition comprising:
(a) a protected nucleophilic compound having the formula

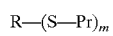

where:
(i) R is a functional group comprising a cosmetically beneficial active capable of being modified to contain at least one thiol ester linkage to Pr,
   a. said active being selected from the group consisting of UV-absorbing compounds, hair conditioning agents, hair repair agents, hair styling agents, hair dyes, coloring agents, brighteners, fluorescent dyes, cross-linkers, and mixtures thereof;
   b. said functional group comprising at least one nucleophilic —SH moiety prior to formation of the S—P bond between S and Pr, at least one halogen-containing electrophilic moiety prior to formation of the C—S bond between R and S, or both;

(ii) Pr is a phosphorus-linked protecting group according the following chemical structure:

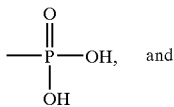 and (iii) m is an integer between 1 and 3; and
(b) a topically acceptable vehicle;
wherein the composition is a topical composition for treating hair.

2. A system comprising:
(a) a topical composition according to claim 1; and
(b) an activating mechanism.

3. A system according to claim 2, wherein the activating mechanism is a pH modifier.

4. A system according to claim 2, wherein the activating mechanism is water.

5. A system according to claim 2, wherein the activating mechanism is an energy source.

6. A system according to claim 2, wherein the activating mechanism is a separate nucleophile.

7. A system according to claim 2, wherein the activating mechanism is pre-reduced hair.

8. A kit comprising:
(a) the system according to claim 3; and
(b) a package comprising a first and second chamber;
wherein the topical composition is packaged in and delivered out of one chamber and the pH modifier is packaged in and delivered out of the second chamber.

9. A hair care composition according to claim 1, wherein the protected nucleophilic compound comprises from about 0.000001% to about 30% of the composition.

10. A hair care composition according to claim 1, wherein the cosmetically beneficial active is selected from the group consisting of coloring agents, hair dyes, and mixtures thereof.

11. A method for attaching a cosmetically beneficial active to hair comprising applying a hair care composition according to claim 1 to hair in need of such treatment.

12. A method for attaching a cosmetically beneficial active to human hair comprising applying a hair care composition according to claim 10 to human hair in need of such treatment.

13. A composition according to claim 1 wherein the cosmetically beneficial active is selected from the group consisting of quaternary ammonium compounds, polyols, esters of fatty acids, esters of mineral oil, intact proteins, modified proteins, amino acids, glycinates, silicone polymers, hydrocarbon based conditioners, polysaccharides, monosaccharides, alkyl cationic conditioning polymers, herb extracts, essential oils, film-forming polymers, styling copolymers comprising silicone macromonomers, cationic styling polymers, hydrocarbon polymers, naphthols, azo derivatives, vegetable dyes, metallized dyes, nitrobenzene dyes, quinone-imine dyes, basic dyes, quaternary dyes, oxidation dyes, derivatives of quaternary ammonium salts of hydroxyethylcellulose, cationic copolymers of acrylic acid and acrylamide, cationic guar polymers, copolymers of vinylimidazolium methochloride and vinylpyrrolidone, polyethylenimines, peptides, enzymes, and mixtures thereof.

14. A composition according to Claim 13 wherein the cosmetically beneficial active is selected from the group consisting of polyols, intact proteins, modified proteins, amino acids, silicone polymers, hydrocarbon based conditioners, alkyl cationic conditioning polymers, film-forming styling polymers, styling copolymers comprising silicone macromonomers, cationic styling polymers, hydrocarbon polymers, naphthols, azo derivatives, vegetable dyes, metallized dyes, nitrobenzene dyes, quinone-imine dyes, basic dyes, quaternary dyes, oxidation dyes, quaternary ammonium salts of hydroxyethylcellulose, cationic copolymers of acrylic acid and acrylamide, cationic guar polymers, copolymers of vinylimidazolium methochloride and vinylpyrrolidone, polyethylenimines, and mixtures thereof.

15. A composition according to claim 14 wherein the cosmetically beneficial active is selected from the group consisting of hydrocarbon groups, silicone polymeric groups, and dye groups.

16. A hair composition according to claim 9, wherein the protected nucleophilic compound comprises from about 0.0001% to about 25% of the composition.

17. A hair composition according to claim 16, wherein the protected nucleophilic compound comprises from about 0.01% to about 20% of the composition.

18. A hair composition according to claim 17, wherein the protected nucleophilic compound comprises from about 0.1% to about 10% of the cpmposition.

19. A hair composition according to claim 18, wherein the protected nucleophilic compound comprises from about 1% to about 5% of the composition.

* * * * *